US00PP21307P2

(12) United States Plant Patent

Klemm et al.

(10) Patent No.: US PP21,307 P2

(45) Date of Patent: Sep. 21, 2010

(54) *PELARGONIUM* PLANT NAMED 'KLEPP08209'

(50) Latin Name: *Pelargonium peltatum*
Varietal Denomination: KLEPP08209

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/383,928

(22) Filed: Mar. 30, 2009

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent L Bell
(74) *Attorney, Agent, or Firm*—Jondle & Associates, P.C.

(57) ABSTRACT

A new cultivar of *Pelargonium* named 'KLEPP08209' particularly characterized by ivy *pelargonium* with a good, stable medium-pink inflorescences, good growth, good branching, and tolerance to heat and rain, is disclosed.

1 Drawing Sheet

Genus and species: *Pelargonium peltatum.*
Variety denomination: 'KLEPP08209'.

BACKGROUND OF THE NEW PLANT

The present invention comprises a new and distinct cultivar of *Pelargonium*, botanically known as *Pelargonium peltatum*, and hereinafter referred to by the cultivar name 'KLEPP08209'. 'KLEPP08209' was discovered as a seedling resulting from a controlled cross in May 2004 in Stuttgart, Germany between the proprietary female *Pelargonium* parent, 'CC 001' (unpatented) and the proprietary male *Pelargonium* parent, 'KLEP04116' (U.S. Plant Pat. No. 18,019). A single plant selection was subsequently chosen for further evaluation and for asexual propagation.

The new cultivar was created in 2004 and first propagated in September 2005 in Stuttgart, Germany and has been asexually reproduced repeatedly by vegetative cuttings in Stuttgart, Germany over a three and one-half year period. 'KLEPP08209' has been found to retain its distinctive characteristics through successive asexual propagations via vegetative cuttings.

Plant Breeder's Rights for this cultivar were applied for in Switzerland on Jun. 19, 2008. 'KLEPP08209' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Ivy *pelargonium* with a good, stable medium-pink inflorescences;
2. Good growth;
3. Good branching; and
4. Good tolerance to heat and rain.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures. The photograph is of a plant about 3-months old taken in Spring 2008 and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPP08209'. The data which define these characteristics were collected from asexual reproductions carried out in Stuttgart, Germany. The plant history was taken on 3-month old plants in 12-cm pots in a greenhouse (glasshouse) in January through April 2008. The plants were pinched once at five weeks. The color readings were determined under natural light. Color references are to the RHS Colour Chart of The Royal Horticultural Society of London (R.H.S.) (2001).

DETAILED BOTANICAL DESCRIPTION

Classification:

*Family.*—Geraniacaea.
*Species.*—*Pelargonium peltatum.*
*Common name.*—*Pelargonium* (Geranium).
*Denomination.*—'KLEPP08209'.

Parentage:

*Female parent.*—The proprietary female *Pelargonium* parent, 'CC 001' (unpatented).
*Male parent.*—The proprietary male *Pelargonium* parent, 'KLEP04116' (U.S. Plant Pat. No. 18,019).

Plant:

*Habit.*—Upright and then becomes trailing.
*Height.*—20.0 cm.
*Spread.*—30.0 cm.
*Life cycle* (*flowering season*).—Spring to autumn.
*Form.*—Round, bushy.
*Time to produce a rooted cutting.*—15 days.

*Time to bloom from propagation.*—Approximately 80 days.

*Lastingness of inflorescence on the plant.*—9 to 13 days.

Stems:

*Stem color.*—RHS 137B.

*Pubescence.*—Very weak, short.

*Pubescence color.*—Greenish white.

*Stem form.*—Round.

*Diameter.*—0.5 cm to 0.6 cm.

*Length.*—8.0 cm to 12.0 cm.

*Internode length.*—1.0 cm to 4.0 cm.

Leaves:

*Arrangement.*—Alternate.

*Shape.*—Kidney-shaped, typical of ivy *pelargonium.*

*Apex.*—Round.

*Base.*—Closed.

*Margin.*—Entire.

*Surface appearance* (*both surfaces*).—Dull.

*Length.*—4.0 cm to 8.0 cm.

*Width.*—5.0 cm to 8.0 cm.

*Color.*—Upper surface: RHS 137B. Lower surface: RHS 137C.

*Surface pubescence* (*both surfaces*).—Absent.

*Petiole.*—Length: 2.0 cm to 8.0 cm. Diameter: Approximately 0.6 cm. Color: RHS 137B.

*Venation pattern.*—Palmate.

*Venation color.—RHS* 137C. Zonation: Very weak. Distance from leaf margin apex to outer edge of zonation: 2.0 cm. Width: Approximately 0.5 to 0.8 cm. Color: RHS 177A.

Inflorescence:

*Type.*—An umbel composed of 5 to 12 flowers.

*Flowering habit,*—Continuous.

*Umbels.*—Number (per plant per growing season): 3 to 4. Depth: 6.0 cm to 7.0 cm. Diameter: 8.0 cm to 9.0 cm.

*Individual florets of the umbel.*—Depth: About 1.0 cm. Diameter: 3.0 cm to 5.0 cm.

Flower buds:

*Cluster shape.*—Round-ovate.

*Length.*—1.0 cm to 4.0 cm.

*Width.*—1.0 cm to 4.0 cm.

*Texture.*—Smooth.

*Bud.*—Shape: Elliptic, shell-shaped. Apex: Acute. Base: Blunt. Margin: Entire, smooth. Color: RHS 137B. Size: Length: 1.0 cm to 1.5 cm. Width: 0.5 cm to 0.8 cm.

Petals:

*Quantity per flower.*—15 to 20.

*Shape.*—Drop-shaped (rain-drop shaped).

*Apex.*—Round.

*Base.*—Obtuse.

*Margin.*—Entire.

*Length.*—2.2 cm.

*Width.*—1.3 cm.

*Texture* (*both upper and lower surfaces*).—Smooth.

*Color of lobes.*—Upper lobes (both upper and lower surfaces): RHS 61D. Lower lobes (both upper and lower surfaces): RHS 62A.

*Fragrance.*—Absent.

Sepals:

*Number per flower.*—5.

*Shape.*—Lanceolate.

*Apex.*—Acute.

*Base.*—Obtuse.

*Margin.*—Entire.

*Color* (*both surfaces*).—RHS 137C.

*Length.*—1.5 cm.

*Width.*—0.4 cm to 0.5 cm.

*Texture.*—Upper surface: Slightly rough. Lower surface: Smooth.

Pedicel:

*Length.*—2.0 cm.

*Diameter.*—0.15 cm.

*Color.*—RHS 137B.

*Texture.*—Slightly rough.

Peduncle:

*Length.*—15.0 cm to 20.0 cm.

*Diameter.*—0.4 cm.

*Color.*—RHS 137C.

*Texture.*—Rough.

Reproductive organs:

*Stamens.*—Anther number (average): 5. Anther length: 0.2 cm. Anther shape: Ovate, elliptic. Filament length: 0.5 cm to 0.7 cm. Filament color: RHS 65D. Pollen amount: Moderate. Pollen color: RHS 35A.

*Pistils.*—Number: 1. Pistil length: 0.3 to 0.7 cm. Stigma color: RHS 58A. Stigma shape: Filamentous. Style length: Small, less than 0.5 cm. Style color: RHS 137D. Ovary arrangement: Central, middle. Ovary color: RHS 136C.

Fruit/seed set: None observed.

Disease and insect resistance: Good, no specific sensitivity observed to diseases and insects.

COMPARISON WITH PARENTAL AND COMMERCIAL CULTIVARS

'KLEPP08209' differs from the female parent, the proprietary female *Pelargonium* parent, 'CC 001' (unpatented) in that 'KLEPP08209' has better branching and is more floriferous than 'CC 001'.

'KLEPP08209' differs from the male parent, the proprietary male *Pelargonium* parent, 'KLEP04116' (U.S. Plant Pat. No. 18,019) in that 'KLEPP08209' has medium-pink inflorescences and a medium growth habit, while 'KLEP04116' (U.S. Plant Pat. No. 18,019) has dark salmon inflorescences and has a very strong growth habit.

'KLEPP08209' differs from the commercial comparison variety Tisprif (U.S. Plant Pat. No. 18,749) in that 'KLEPP08209' has longer leaves (4.0 cm to 8.0 cm), a longer peduncle (15.0 cm to 20.0 cm), and smaller petals (2.2 cm length and 1.3 cm width), while 'Fisprit' has shorter leaves (3.2 cm to 3.7 cm), a shorter peduncle (14.3 cm), and larger petals (3.3 cm to 3.6 cm length and 2.0 cm to 2.2 cm width). In addition, the upper petals of 'KLEPP08209' are RHS 61D (medium pink); while the upper petals of 'Fisprif' are from RHS 65B to RHS 65C or RHS 75B (light bluish-pink) with distinctive markings of RHS N57B (red-purple) spots and RHS 67A veins near the base.

I claim:

1. A new and distinct cultivar of *Pelargonium* plant named 'KLEPP08209' as shown and described herein.

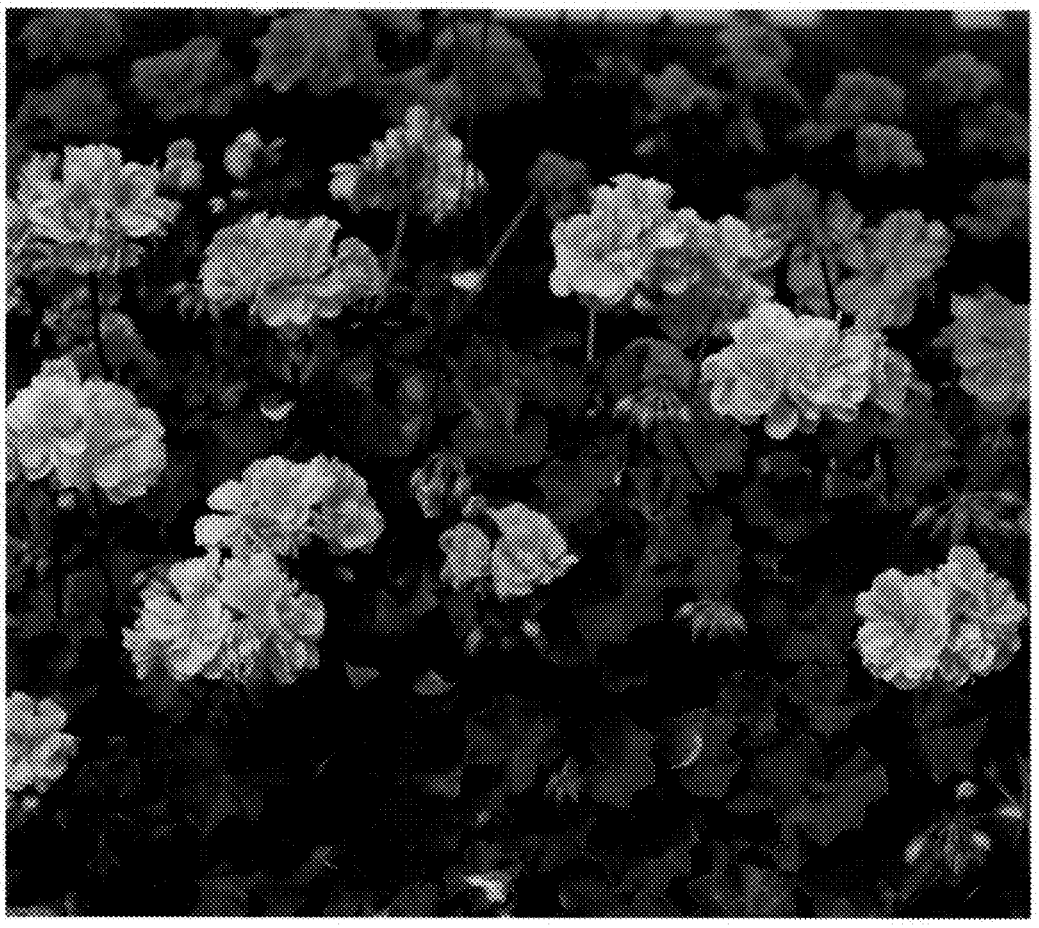

* * * * *